United States Patent
Laaksonen et al.

(10) Patent No.: US 7,611,902 B2
(45) Date of Patent: Nov. 3, 2009

(54) DIAGNOSTIC METHOD FOR MYOPATHY

(75) Inventors: Reijo Laaksonen, Lempäälä (FI); Matej Oresic, Espoo (FI); Terho Lehtimäki, Tampere (FI); Hannu Päivä, Tampere (FI)

(73) Assignee: Zora Biosciences Oy, Espoo (FI)

( * ) Notice: Subject to any disclaimer, the term of this patent is extended or adjusted under 35 U.S.C. 154(b) by 184 days.

(21) Appl. No.: 11/761,427

(22) Filed: Jun. 12, 2007

(65) Prior Publication Data

US 2008/0003684 A1    Jan. 3, 2008

Related U.S. Application Data

(60) Provisional application No. 60/872,495, filed on Dec. 4, 2006, provisional application No. 60/812,602, filed on Jun. 12, 2006.

(51) Int. Cl.
*G01N 33/48* (2006.01)
*G01N 33/92* (2006.01)

(52) U.S. Cl. ............... 436/63; 436/71; 436/94; 435/6; 435/975; 536/23.1

(58) Field of Classification Search ............ 436/63, 436/71, 94; 435/6, 975; 536/23.1
See application file for complete search history.

(56) References Cited

U.S. PATENT DOCUMENTS

2003/0224470 A1* 12/2003 Phillips ............... 435/7.92
2005/0009005 A1    1/2005 Watkins
2007/0202518 A1* 8/2007 Ruano et al. ............... 435/6

FOREIGN PATENT DOCUMENTS

WO    WO03/005628    1/2003
WO    2007/061995  * 5/2007

OTHER PUBLICATIONS

Laaksonen et al. PLoS One, vol. e97, issue 1, Dec. 2006, pp. 1-9.*
"An Assessment of Statin Safety by Muscle Experts," Thompson et al., The American Journal of Cardiology (www.AJConline.org), vol. 97(8A), Apr. 17, 2006.
"High-dose statins and skeletal muscle metabolism in humans: A randomized, controlled trial," Hannu Paiva et al., Clinical Pharmacology & Therapeutics, Jul. 2005.

* cited by examiner

*Primary Examiner*—Maureen M Wallenhorst
(74) *Attorney, Agent, or Firm*—Young & Thompson

(57) ABSTRACT

This invention provides a diagnostic method for determining statin induced myopathy. The method is especially applicable for determining warnings, early signs and also symptomatic myopathy. The method includes collecting a lipidomic profile from a biological sample such as blood or serum and comparing the obtained lipidomic profile to reference lipidomic markers. The reference lipidomic markers have been established by combining a pro-inflammatory muscle tissue gene expression profile with a lipidomic profile associated with high dosage statin treatment. This invention also relates to a kit for performing a method for determining statin induced myopathy.

11 Claims, 3 Drawing Sheets

DIAGNOSTIC METHOD FOR MYOPATHY

FIELD OF THE INVENTION

This invention relates to a diagnostic method for determining statin induced myopathy. The method is especially applicable for determining warnings, early signs and also symptomatic myopathy. The method includes collecting and comparing lipid biomarker patterns to reference lipidomic markers. The method also includes chemometric modelling and statistical analysis of the biomarker patterns. This invention further relates to a kit for performing a diagnostic method for determining statin induced myopathy.

BACKGROUND OF THE INVENTION

High levels of blood cholesterol is one of the major risk factors leading to atherosclerosis and cardiovascular diseases. Elevated cholesterol levels can be clinically lowered with 3-hydroxy-3-methylglutaryl-coenzyme A reductase inhibitors, collectively called statins. Statins have been showed in large clinical trial to effectively lower cholesterol blood levels. A vast amount of different statins exists today. High cholesterol values are very common in Europe and in USA and the use of statins to lower cholesterol values is increasing drastically. In EU-countries statin use increased from 1997 to 2002 by 30% on average.

Recent clinical data show that statin therapy is associated with adverse effects. The most prevalent and important adverse effect associated with statin therapy is myopathy. Myopathy is a collective term for various muscle related problems, such as muscle pain (myalgia), weakness and cramps (Paul D. Thompson et al, Am J Cardiol 2006, 97 [suppl]: 69C-76C). The exact mechanism for statin induced myopathy is still unclear. A recent study showed that clinically acceptable doses of atorvastatin and simvastatin resulted in lowered levels of plasma ubiquinone. Ubiquinone is a coenzyme that is involved in mithocondrial electron transport and is therefor involved in tissue energy metabolism. Statins such as atorvastatin and simvastatin clearly have an effect on skeletal muscle (Päivä et al, Clin Pharmacol Ther 2005; 78:60-8).

Metabolomics is a discipline dedicated to the systematic study of small molecules (i.e., metabolites) in cells, tissues, and biofluids. Metabolites are the end products of cellular regulatory processes, and their levels can be regarded as the amplified response of biological systems to genetic or environmental changes. Clinicians have relied for decades on a small part of the information contained in the metabolome, for example measuring glucose to monitor diabetes and measuring cholesterol for cardiovascular health. New sophisticated metabolomic analytical platforms and informatic tools have already been developed that afford extended and sensitive measurement of the metabolome.

Lipids are known to play an important role as structural components (e.g., cell membranes), energy storage components, and as signalling molecules. Lipids are broadly defined as hydrophobic or amphipathic small molecules that may originate entirely or in part by carbanion based condensation of thioesters, and/or by carbocation based condensation of isoprene units. Lipidomics can be considered as a sub-field of metabolomics which aims to elucidate the biological processes in the context of lipids by measuring and characterizing the extended lipid profiles at the molecular level (lipidomic profiles). Traditional clinical lipid measures quantify total amounts of triglycerides, cholesterol, or lipoproteins. However, serum lipid profile is more complex at the molecular level. Current lipidomics platforms enable quantitative characterization of 100 s of diverse lipid molecular species across multiple lipid classes such as sphingolipids, phospholipids, sterol esters, acylglycerols, sterols, bile acids, fatty acids, eicosanoids, and steroids.

Myopathy is today mainly diagnosed from the symptoms of the patient. Elevated creatine kinase (CK) levels can be used for testing patients with muscle symptoms. However, CK levels can be elevated due to other reasons such as exercise, and is not a reliable biomarker for statin induced myopathy. At the moment there is no diagnostic method or clinical test for diagnosing asymptomatic myopathy. Furthermore it is impossible to estimate the risk of a patient to develop myopathy when undergoing statin therapy. The present invention discloses a diagnostic method for determining the risk and early signs of statin induced myopathy.

SUMMARY OF THE INVENTION

This invention discloses a method for determining statin induced myopathy comprising the steps:

a) providing a biological sample from an individual prior to or during statin treatment, b) collecting a lipidomic profile from said biological sample, c) comparing said collected lipidomic profile to reference lipidomic markers, wherein said reference lipidomic markers have been established by combining a pro-inflammatory gene expression profile with a lipidomic profile connected to high dosage statin treatment.

The method is especially useful for determining the risk or early warning signs of statin induced myopathy. The method is also useful for determining statin induced myopathy in individuals showing clinical symptoms of myopathy.

Another aspect of the invention is to provide a kit for determining statin induced myopathy.

DETAILED DESCRIPTION OF THE INVENTION

Figure 1:
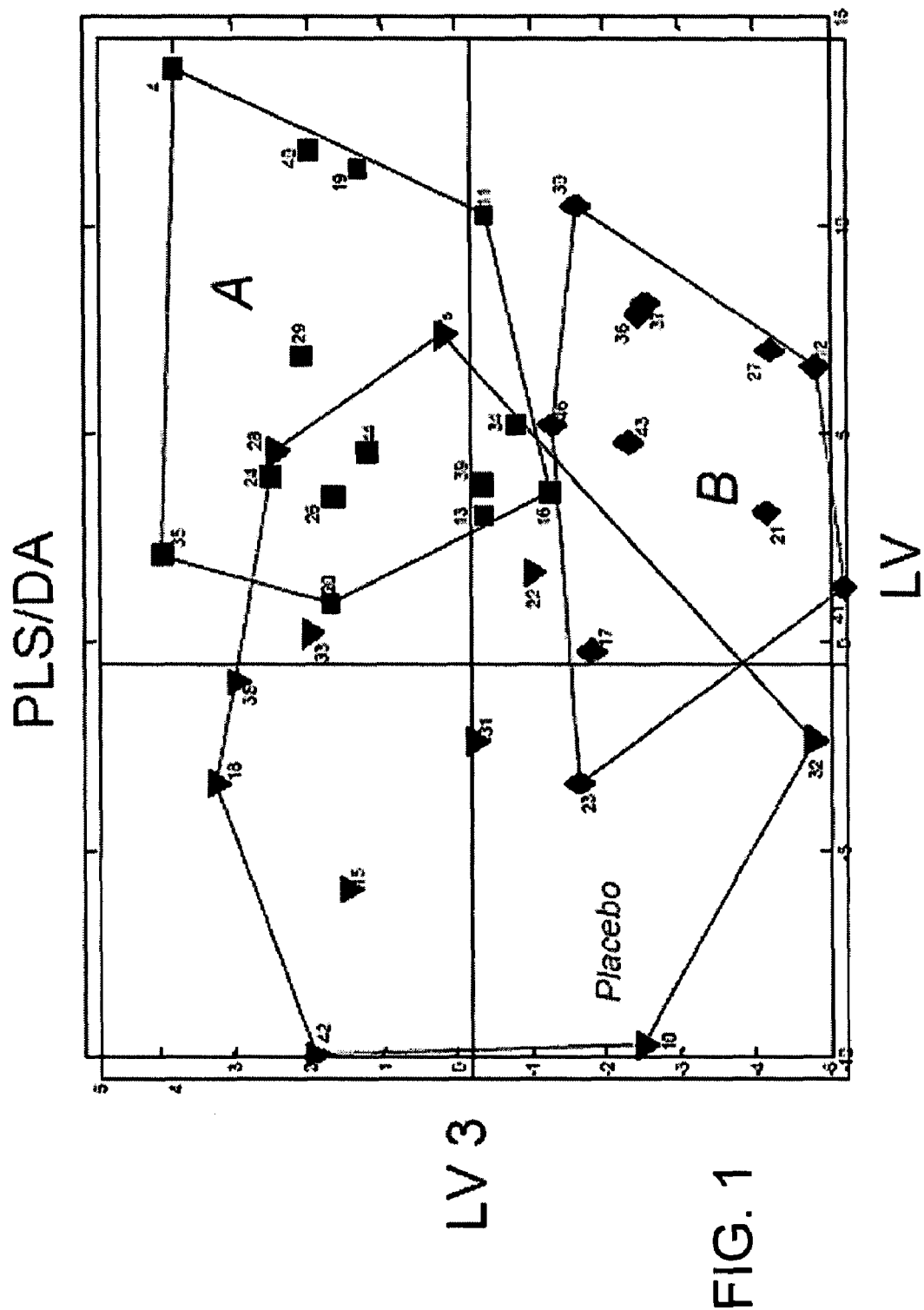
FIG. 1 denotes partial least squares discriminant analysis (PLS/DA) of serum lipidomics data. Results after 8 week treatment from placebo (N=11), atorvastatin (N=14) (A), and simvastatin (N=12) (B) groups, with 132 identified lipid species included in analysis as variables. For each molecular species and each subject, its level after the 8 week treatment period was scaled by subtracting its median level across all subjects prior to treatment and divided by corresponding standard deviation. Four latent variables were used in the model ($Q^2$=0.46). The labels are patient ID numbers. The lines outlining different groups are shown as a guide. The scores for Latent Variables (LV) 1 and 3 reveal serum lipid changes specific to the statin treatment (LV1) as well as statin-specific changes (LV3).

The objective of the present invention is to provide an early stage biomarker for statin induced myopathy. The early stage biomarker can be used for determining a risk of developing myopathy as a result of cholesterol lowering treatment with statins before any symptoms of actual myopathy occurs. The biomarker can also be used for early warning signs of statin induced myopathy. The cholesterol lowering medication can be adjusted when early sign of myopathy is detected. Further the biomarkers can be used to determine statin induced myopathy, when clinical symptoms of myopathy already occurs. The inventors have now surprisingly found that lipidomic biomarkers can be used as biomarkers for statin induced myopathy.

The present invention provides a method for determining the risk and early warning signs for a patient to develop statin induced myopathy. The method is based on comparison of the established lipid profile from an individual to a reference lipidomic markers. The reference lipidomic markers are created by combining gene expression analysis data with serum lipidomics data. Gene expression profiles associated with high dose statin treatment have been detected by whole genome microarray analysis of muscle biopsies. The information from the microarray analysis and lipidomics analyses are combined and statistically modified to provide lipidomic markers useful for statin induced myopathy.

This invention discloses a method for determining myopathy. The method is useful for determining early signs of myopathy prior to any clinically observable signs occur. The benefits of the current method is that the statin treatment can be adjusted or stopped before any physical myopathy symptoms occur.

Another aspect of the current invention is to provide a method for determining statin induced myopathy in individuals already suffering from clinical myopathy symptoms. The method according to the current invention can be used as a biochemical diagnostic method for myopathy in patients already experiencing muscle pains and other symptoms of myopathy. The method can be used as a verification diagnostic method besides other clinical diagnosis of myopathy. Creatine kinase (CK) levels are usually measured in patients suspected of suffering from myopathy. The disclosed method can be used in parallel with CK level measurements. CK levels are not reliable biomarkers for myopathy since CK levels can be high because of e.g. small muscle injuries after exercise and physical activity. The current inventions provides more reliable biomarkers for statin induced myopathy than CK levels.

The current invention provides a method for determining statin induced myopathy comprising the steps:

a) providing a biological sample from an individual prior to or during statin treatment, b) collecting a lipidomic profile from said biological sample, c) comparing said collected lipid profile to reference lipidomic markers, wherein said reference lipidomic markers have been established by combining a pro-inflammatory gene expression profile with a lipidomic profile connected to high dosage statin treatment.

The difference between the collected lipidomic profile and the reference lipidomic markers indicates or is associated with statin induced myopathy. The difference between the collected lipidomic profile and the reference lipidomic markers can also be used for determining a risk of or susceptibility for developing statin induced myopathy.

The method according to the current invention can be used for determining a risk to develop statin induced myopathy as a result of statin treatment.

Further the method according to the current invention can be used for determining early warning signs of statin induced myopathy. The early warning signs can be determined before actual symptoms of myopathy occurs in the individual.

Still further the method according to the current invention can be used for determining statin induced myopathy in individuals already showing signs of myopathy. The current method can be a biochemical verification of clinically diagnosed myopathy.

The biological sample can be whole blood, serum, plasma sample or a tissue sample. Taking a blood sample of a patient is a part of normal clinical practice. The blood sample can be taken in connection with e.g. measuring the cholesterol levels in the patients. The collected blood sample can be pre-pared and serum or plasma can be separated with techniques well known for a person skilled in the art.

Collecting a lipidomic profile from said biological sample can be performed with various chemical and high resolution analytical techniques. Suitable analytical techniques include but are not limited to mass spectrometry and nuclear resonance spectroscopy. Any high resolution technique capable of re-solving individual lipids or lipid classes and provide structural information of the same can be used to collect the lipid profile from the biological sample.

Collecting the lipidomic profile with mass spectrometry (MS) is one embodiment of the current invention. The MS instrument can be coupled to a high performance separation method such as HPLC or HPLC.

The analytical technique used for collecting the lipid profile should be able to quantify or measure either the exact amount or at least a relative amount of the individual lipids or lipid classes. The amount of the individual lipids or lipid classes in the collected lipidomic profile is used when comparing the collected lipid profile to the reference lipidomic biomarkers.

The reference lipidomic biomarkers can be established from the same individual receiving the statin treatment or it can be from a generalised population. If the same individual is used to create the reference lipidomic marker, then a sample is collected from the individual prior to statin treatment. The reference lipidomic marker is then created from that first lipid profile of that individual. This lipidomic marker is used as a base-line or starting point. A series of lipidomic profiles can be collected during statin treatment. These lipidomic profiles are then compared with the reference lipidomic marker that was created prior to statin treatment.

The reference lipidomic markers can also be created from a generalized population. If a generalized population is used then several lipid profiles from a population are combined and the lipidomic marker is created from this combination.

Preferably, the reference lipidomic markers are one or more lipid(s) selected from the lipids presented in table 1, more preferable in table 2.

The reference lipidomic marker is created by combining gene expression data with lipidomics analysis as described below. The levels or amounts of the individual lipids or lipid classes are compared to the levels or amounts of the individual lipids or lipid classes in the reference lipidomic biomarkers for determining statin induced myopathy.

TABLE 1

| | |
|---|---|
| 1 | GPCho(0:0/16:0) |
| 2 | GPCho(16:0/0:0) |
| 3 | GPCho(O-16:2) |
| 4 | GPCho(0:0/18:0) |
| 5 | GPCho(18:0/0:0) |
| 6 | GPCho(0:0/18:1) |
| 7 | GPCho(18:1/0:0) |
| 8 | GPCho(0:0/18:2) |
| 9 | GPCho(18:2/0:0) |
| 10 | GPCho(18:3/0:0) |
| 11 | GPCho(0:0/20:3) |
| 12 | GPCho(20:3/0:0) |
| 13 | GPCho(20:4/0:0) |
| 14 | GPCho(20:4/0:0) |
| 15 | GPCho(22:6/0:0) |
| 16 | Cer(d18:1/22:0) |
| 17 | DG(36:2) |
| 18 | DG(44:12) |
| 19 | GPCho(32:0) |
| 20 | GPCho(O-32:0) |
| 21 | GPCho(32:1) |
| 22 | GPCho(O-32:1) |
| 23 | GPCho(34:1) |
| 24 | GPCho(O-34:1) |
| 25 | GPCho(34:2) |
| 26 | GPCho(O-34:2) |
| 27 | GPCho(34:3) |
| 28 | GPCho(O-34:3) |
| 29 | GPCho(36:0) |
| 30 | GPCho(36:1) |
| 31 | GPCho(36:1) |
| 32 | GPCho(36:2) |
| 33 | GPCho(O-36:2) |
| 34 | GPCho(36:3) |
| 35 | GPCho(O-36:3) |
| 36 | GPCho(O-36:3) |
| 37 | GPCho(36:4) |
| 38 | GPCho(36:4) |
| 39 | GPCho(O-36:4) |
| 40 | GPCho(36:5) |
| 41 | GPCho(36:5) |
| 42 | GPCho(O-36:5) |
| 43 | GPCho(38:2) |
| 44 | GPCho(38:3) |
| 45 | GPCho(38:4) |
| 46 | GPCho(38:4) |
| 47 | GPCho(38:4) |
| 48 | GPCho(O-38:4) |
| 49 | GPCho(38:5) |
| 50 | GPCho(O-38:5) |
| 51 | GPCho(38:6) |
| 52 | GPCho(38:6) |
| 53 | GPCho(O-38:6) |
| 54 | GPCho(38:7) |
| 55 | GPCho(O-38:7) |
| 56 | GPCho(40:4) |
| 57 | GPCho(O-40:4) |
| 58 | GPCho(40:6) |
| 59 | GPCho(40:7) |
| 60 | SM(d18:0/16:0) |
| 61 | SM(d18:0/18:0) |
| 62 | SM(d18:0/24:0) |
| 63 | SM(d18:1/16:0) |
| 64 | SM(d18:1/16:1) |
| 65 | SM(d18:1/18:0) |
| 66 | SM(d18:1/18:3) |
| 67 | SM(d18:1/20:0) |
| 68 | SM(d18:1/22:0) |
| 69 | SM(d18:1/22:1) |
| 70 | SM(d18:1/24:0) |
| 71 | SM(d18:1/24:1) |
| 72 | GPEtn(36:1) |
| 73 | GPEtn(36:2) |
| 74 | GPEtn(38:1) |
| 75 | GPEtn(O-38:1) |
| 76 | GPEtn(38:2) |
| 77 | GPEtn(38:4) |
| 78 | GPEtn(O-38:5) |
| 79 | GPEtn(O-38:6) |

TABLE 1-continued

| | |
|---|---|
| 80 | GPEtn(40:4) |
| 81 | GPEtn(42:6) |
| 82 | GPSer(36:0) |
| 83 | ChoE(18:0) |
| 84 | ChoE(18:1) |
| 85 | ChoE(18:2) |
| 86 | ChoE(20:4) |
| 87 | ChoE(20:5) |
| 88 | TG(46:0) |
| 89 | TG(46:1) |
| 90 | TG(46:2) |
| 91 | TG(48:0) |
| 92 | TG(48:0) |
| 93 | TG(48:1) |
| 94 | TG(48:1) |
| 95 | TG(48:2) |
| 96 | TG(48:3) |
| 97 | TG(49:1) |
| 98 | TG(50:0) |
| 99 | TG(50:0) |
| 100 | TG(50:1) |
| 101 | TG(50:1) |
| 102 | TG(50:2) |
| 103 | TG(50:2) |
| 104 | TG(50:2) |
| 105 | TG(50:3) |
| 106 | TG(50:4) |
| 107 | TG(51:1) |
| 108 | TG(51:2) |
| 109 | TG(51:3) |
| 110 | TG(52:0) |
| 111 | TG(52:1) |
| 112 | TG(52:1) |
| 113 | TG(52:2) |
| 114 | TG(52:2) |
| 115 | TG(52:3) |
| 116 | TG(52:4) |
| 117 | TG(52:5) |
| 118 | TG(54:2) |
| 119 | TG(54:2) |
| 120 | TG(54:3) |
| 121 | TG(54:3) |
| 122 | TG(54:4) |
| 123 | TG(54:4) |
| 124 | TG(54:5) |
| 125 | TG(54:6) |
| 126 | TG(56:5) |
| 127 | TG(56:5) |
| 128 | TG(56:6) |
| 129 | TG(56:7) |
| 130 | TG(56:8) |
| 131 | TG(56:9) |
| 132 | TG(58:8) |

GPCho = phosphatidylcholine
Cer = ceramide
DG = diacylglycerol
SM = sphingomyelin
GPEtn = phosphatidylethanolamine
ChoE = cholesterol ester
TG = triacylglycerol In order to understand the pathways associated with statin response in muscle, we performed whole genome microarray analysis in muscle biopsies. The biopsy samples were taken from three groups of individuals. The groups were individuals receiving only placebo, individuals receiving atorvastatin treatment and individuals receiving simvastatin treatment. Microarray experiments were performed in individuals who did not have any observed side effects such as muscle pain or creatine kinase elevations as a result of statin treatment.

TABLE 2

| | |
|---|---|
| 1 | GPCho(34:3) |
| 2 | GPCho(36:0) |

TABLE 2-continued

| | |
|---|---|
| 3 | GPCho(36:3) |
| 4 | GPCho(38:2) |
| 5 | GPCho(38:3) |
| 6 | GPCho(38:4) |
| 7 | GPCho(38:5) |
| 8 | GPCho(O-38:5) |
| 9 | GPCho(38:6) |
| 10 | GPCho(38:7) |
| 11 | GPCho(O-38:7) |
| 12 | GPCho(40:6) |
| 13 | SM(d18:0/16:0) |
| 14 | SM(d18:0/18:0) |
| 15 | SM(d18:1/18:0) |
| 16 | SM(d18:1/22:0) |
| 17 | GPEtn(38:1) |
| 18 | GPEtn(40:4) |
| 19 | ChoE(18:0) |
| 20 | ChoE(18:2) |
| 21 | TG(54:2) |
| 22 | TG(54:3) |
| 23 | TG(56:5) |

GPCho = phosphatidylcholine
SM = sphingomyelin
GPEtn = phosphatidylethanolamine
ChoE = cholesterol ester
TG = triacylglycerol First a single-gene analysis was performed to reveal affected genes in muscle by statin treatment. Only modest changes were recorded in the atorvastatin group as expression of five genes was observed to change significantly during the intervention. In the simvastatin group expression of genes changed significantly. Based on a hierarchical cluster analysis 20 genes were selected further RT-PCR control in order to identify a gene expression based fingerprint for statin effect on human skeletal muscle.

As the recorded differences in single gene expressions in general were rather modest, we performed a gene set enrichment analysis (GSEA) to illuminate affected metabolic pathways that may not have appeared in the single gene analyses. In the GSEA no pathways appeared to be affected significantly in the atorvastatin or placebo group according to the criteria (FDR<0.25). Interestingly, in the simvastatin group 143 pathways were re-corded to be up-regulated (FDR<0.25) during high dose simvastatin treatment. Due to the large number of affected pathways we limited our systematic analyses to the most affected pathways (FDR<0.10).

In order to investigate how the high dose statin treatment affects the plasma lipid profiles and whether the metabolism changes found in skeletal muscle are reflected in the plasma lipidome, we applied the lipidomics analysis. Samples subjects, prior and after the intervention from placebo, simvastatin, and atorvastatin groups were analyzed. Following the data processing, total 132 lipid molecular species were identified and included in the data analysis.

Figure 2:
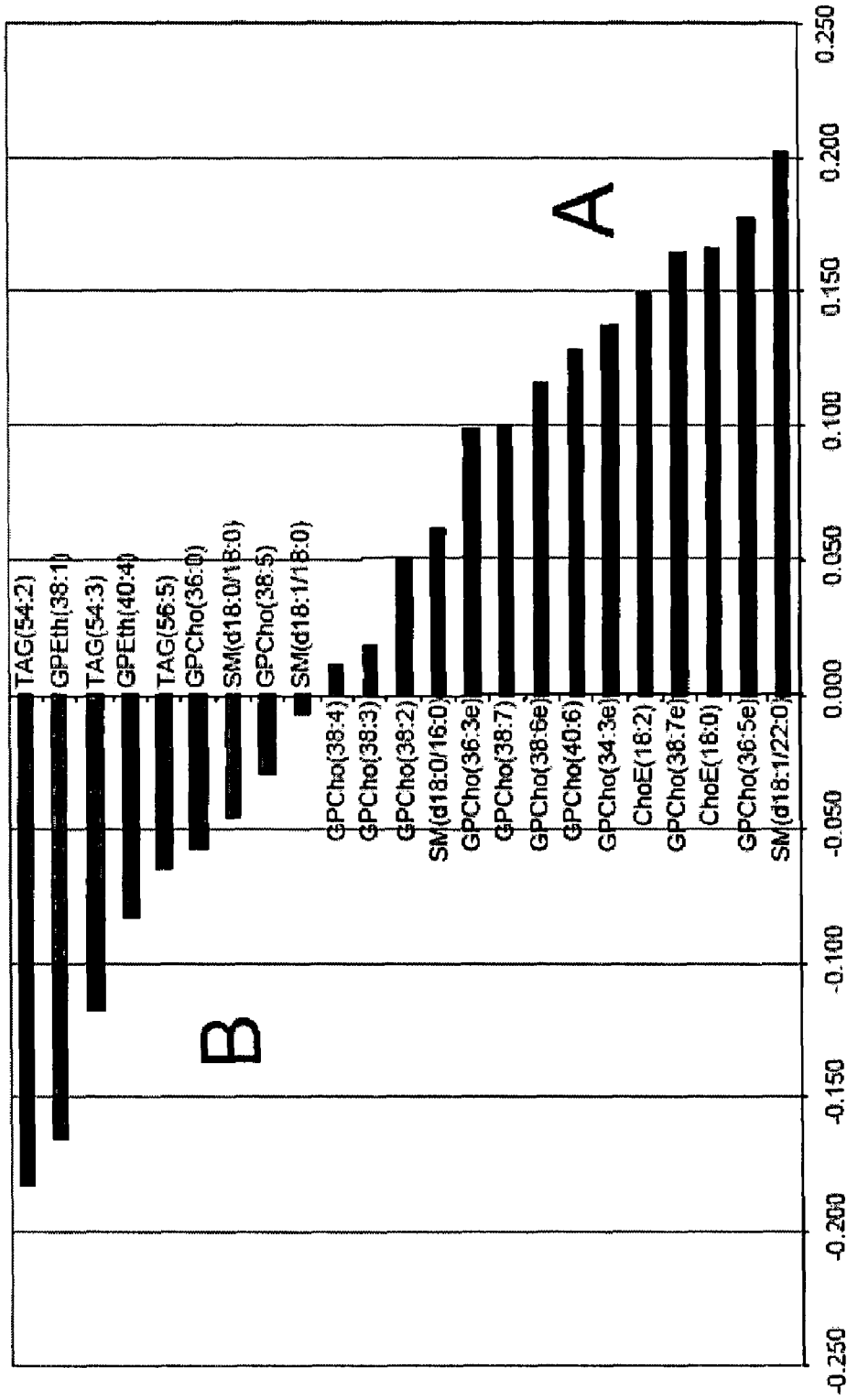
FIG. 2 denotes loadings on LV3 for most important lipids in simvastatin (B) or atorvastatin (A) groups selected by VIP analysis from FIG. 1. Only lipids for which at least one of the two groups has VIP value greater than 2 are shown.

Partial Least Squares Discriminant Analysis (PLS/DA) revealed drug-specific changes in lipid profiles (FIG. 1). The differences along the first latent variable (LV1), associated with changes due to statin treatment common to the two drugs, are expectedly associated with lowering of triacylglycerols and cholesterol esters in the statin intervention groups. The differences between the simvastatin and atorvastatin lipid profiles were found in the third latent variable (LV3). Following VIP (variable importance in the projection) analysis, the most important lipid species were identified for each intervention group. The list of loadings in direction of atorvastatin-simvastatin differences (LV3) for most important lipids in simvastatin and atorvastatin groups is shown in FIG. 2. Notably, the main plasma lipid profile differences between the two statins appear lipid-class specific, with upregulation of several phosphatidylethanolamines and long chain triacylglycerols, and downregulation of ether phosphatidylcholine and cholesterol esters in the simvastatin group.

Gene expression analysis revealed upregulated pathways in skeletal muscle associated with inflammation and mitochondrial damage in the high dose simvastatin intervention group. We investigated if any of these changes are associated with the differences observed in the serum lipidome.

Figure 3:
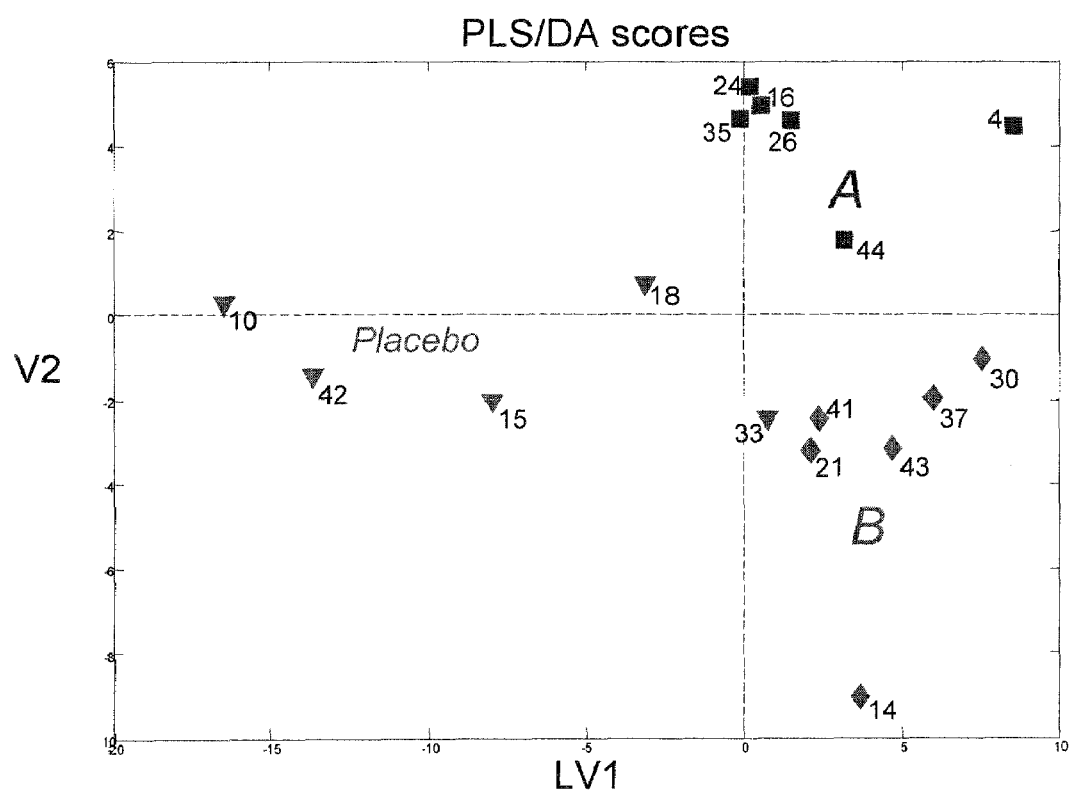
FIG. 3 denotes PLS/DA analysis on combined muscle gene expression and serum lipid data. Results after intervention for the subjects from placebo (N=5), atorvastatin (N=6) (A), and simvastatin (N=6) (B) groups. Total 38 genes from four enriched pathways and 132 lipids were included in the analysis as variables. Data was autoscaled prior to multivariate analysis. Three latent variables were used in the model ($Q^2$=0.50). The labels are patient ID numbers. The PLS/DA score plot reveals treatment-specific differences between the treatments are observed in molecular profiles after intervention.

We selected a subset of genes based on GSEA analysis. Genes from PLC, tubby, eicosanoid biosynthesis, and sodd pathways were chosen, which were ranked 2nd to 5th based on FDR q-value. Total 38 gene expression profiles were included along with 132 lipids. The PLS/DA analysis on combined muscle gene expression and plasma lipid profile data revealed clear differences between the three treatment groups (FIG. 3). The loadings reveal that the simvastatin group after treatment is primarily associated with the changes in multiple genes from eicosanoid synthesis pathways as well as changes in multiple phosphatidylethanolamine and sphingomyelin molecular species. Since the Partial Least Squares analysis maximizes the product of variance matrix of measured variables (e.g. combined gene expression and lipid profile data) and correlation of measured data with properties of interest (e.g. treatment groups), these results clearly show that in the simvastatin group there is a high degree of correlation between the upregulated genes (pathways) and lipidomic markers.

Another aspect of the current invention is to provide a kit for performing a method for determining statin induced myopathy. The kit comprises reference lipids to form the lipidomic reference biomarkers and necessary reagents.

Lipids from the lipidomic analysis were named according to Lipid Maps (http://www.lipidmaps.org). For example, lysophosphatidylcholine with 16:0 fatty acid chain was named as monoacyl-glycerolphosphocholine GPCho(16:0/0:0). In case the fatty acid composition was not determined, total number of carbons and double bonds was marked. For example a phosphatidylcholine species GPCho(16:0/20:4) is represented as GPCho(36:4). However GPCho(36:4) could represent other molecular species such as GPCho(20:4/16:0) or GPCho(18:2/18:2). Such mass isomers may be separated chromatographically.

The following examples illustrates the invention but are not intended to limit the scope of the invention

EXAMPLES

Patients for the Gene Expression and Lipidomic Analyses

Plasma samples from 37 subjects of an earlier study (8) focusing on the effect of high dose statin treatment on skeletal muscle metabolism were used for plasma lipidome analysis. The subjects aged between 31 and 69 years and their average serum total cholesterol concentration was 5.9±0.9 mmol/L and serum triglycerides below 4.5 mmol/L. Muscle specimens from eighteen age matched men being treated either with atorvastatin (n=6), simvastatin (n=6) or placebo (n=6) were selected for whole genome wide expression analysis.

The study patients had never been treated with statins before. They were instructed to adhere to their normal diet during the study. Patients with familial hypercholesterolemia and patients with serum total cholesterol >7.0 mmol/L in the initial screening were excluded. Other exclusion criteria were: use of concurrent lipid altering medication or antioxidant vitamins, renal or hepatic dysfunction, and use of medication known to affect metabolism of atorvastatin or simvastatin. The study protocol was accepted by the Ethics Committee of the Tampere University Hospital and written informed consents were obtained from all participants.

Example 1

Gene Expression Analysis

Gene Expression

Microarray experiments were performed by using Sentrix® Human-6 Expression BeadChips analyzing over 46 000 known genes, gene candidates and splice variants (Illumina, San Diego, Calif., USA) according to given instructions. The biopsy samples were homogenized using Ultra-Turrax (IKA Turrax T8/S8N-5G, IKA-Werke, Staufen, Germany). The total RNA was extracted using TRIzol (#15596-018, Invitrogen Corporation, Carlsbad, Calif.), DNase treatment and a second RNA purification by Qiagen kits (#74106, and, #79254, Qiagen GmbH, Hilden, Germany), all by given instructions.

A 200 ng aliquote of total RNA from each sample were amplified to cDNA using Ambion's Illumina RNA Amplification kit following the instructions (cat no I1755, Ambion, Inc., Austin, Tex., USA). In vitro transcripiton (IVT) reaction of cDNA to cRNA was performed overnight (14 h) including biotin-11-dUTP (PerkinElmer, cat no PC 3435-0402-Biotin-11-dUTP, >95%, NEL539001EA, PerkinElmer Life And Analytical Sciences, Inc., Boston, Mass., USA) for labelling the cRNA product. Both before and after the amplifications the RNA/cRNA concentrations were checked with Nanodrop ND-1000 spectrophotometer (Nanodrop Technologies, Wilmington, Del., USA) and RNA/cRNA quality was controlled by BioRad's Experion Automated Electrophoresis System and RNA StdSens Analysis Kit (BioRad Laboratories, Inc., Hercules, Calif., USA).

1500 ng of each sample cRNA was hybridized to Illumina's Sentrix® Mouse-6 Expression BeadChip arrays (Illumina, Inc., San Diego, Calif., USA) at 55° C. overnight (18 h) following the Illumina Whole-Genome Gene Expression Protocol for BeadStation (Doc. # 11176837 Rev. F, Illumina Inc.). Hybridized biotinylated cRNA was detected with 1 μg/ml Cyanine-3-streptavidine (Amersham Biosciences #146065). BeadChips were scanned with Illumina BeadArray Reader.

Raw intensity data obtained from the Illumina platfrom were normalized with Inforsense Knowledge Discovery Environment (Inforsense, London, UK) using non-linear cubic-spline normalization. The Inforsense KDE platform was also used to conduct single-gene analysis including fold-change calculations and filtering the probes.

According to the used selection criteria (1.5-fold change and p-value <0.05) expression of one gene was significantly changed in the placebo group. Only modest changes were recorded in the atorvastatin group as expression of five genes was observed to change significantly during the intervention. In the simvastatin group, however, expression of 111 genes changed significantly. Twenty-six genes were down-regulated and 85 genes were up-regulated.

Example 2

RT-PCR Analysis

Based on a hierarchical cluster analysis (described in Example 1) 20 genes were selected for further RT-PCR control in order to identify a gene expression based fingerprint for statin effect on human skeletal muscle.

The microarray expression results recorded in the simvastatin group (n=5, for one case there was not enough muscle RNA for PCR) were verified by RealTime Quantitative TaqMan PCR. Previously purified cRNA was used as starting material for cDNA synthesis. A 1000 ng-18 μl aliquote of cRNA was mixed with 1 μl Promega Random Primer (C1181, Promega U.S., Madison, Wis., USA) and incubated in +70° C. for 10 min. The following reagents were added leading to 25 μl total reaction volume: 1 μl of 10 μM dNTP blend (F09892, Applied Biosystems, Foster City, Calif., USA), 1 μl of Promega M-MLV Reverse Transcriptase 200 U/μl (M3682) and 4 μl of M-MLV $R_T$ 5× reaction buffer. Finally the incubations were performed in the following order: 10 min in RT, 50 min in 45° C., and, 10 min in 70° C. 10 μl volume was used for PCR reaction, consisting of 2 μl aliquote of 1:10 diluted cDNA sample, and, Abgene ABsolute 2×QPCR ROX mix (AB-1139, Abgene, Epsom, UK). The primer concentrations were 300 nM, probe concentrations for Universal Probe Library (Exiqon, Vedbaek, Denmark) probes 100 nM and for ordinary long probes 200 nM. Finally the PCR reactions were performed in rtPCR system (ABI Prism 7700 Sequence Detection System, Applied Biosystems) having the following PCR procedure: 95° C. for 15 min, and 40 cycles of 95° C. for 15 s and 60° C. for 1 min.

The RT-PCR analyses revealed that 5 genes seemed to be the most sensitive candidate markers of an early pre-myopathic statin effect in the simvastatin group: ALOX5AP (+3.6-fold, p=0.041), CCL5 (+11.9-fold, p=0.011), COL3A1 (+27.1-fold, p=0.026), MYL5 (+8.0-fold, p=0.021), MYBPH (+49.0-fold, p=0.027).

Example 3

Lipidomics Analysis of Plasma

An aliquot (10 ml) of an internal standard mixture containing 11 lipid classes, and 0.05M sodium chloride (10 ml) was added to plasma samples (10 ml) and the lipids were extracted with chloroform/methanol (2:1, 100 ml). After vortexing (2 min), standing (1 hour) and centrifugation (10000 RPM, 3 min) the lower layer was separated and a standard mixture containing 3 labeled standard lipids was added (10 ml) to the extracts (the internal and external standards are listed in the Supplement). The sample order for LC/MS analysis was determined by randomization.

Lipid extracts were analysed on a Waters Q-T of Premier mass spectrometer combined with an Acquity Ultra Performance LC™ (HPLC). The column, which was kept at 50° C., was an Acquity HPLC™ BEH C18 10×50 mm with 1.7 mm particles. The binary solvent system included A. water (1% 1M $NH_4Ac$, 0.1% HCOOH) and B. LC/MS grade (Rathburn) acetonitrile/isopropanol (5:2, 1% 1M $NH_4Ac$, 0.1% HCOOH). The gradient started from 65% A/35% B, reached 100% B in 6 min and remained there for the next 7 min. The total run time including a 5 min re-equilibration step was 18 min. The flow rate was 0.200 ml/min and the injected amount 0.75 ml. The temperature of the sample organizer was set at 10° C.

The lipid profiling was carried out on Waters Q-T of Premier mass spectrometer using ESI+mode. The data was collected at mass range of m/z 300-1200 with a scan duration of 0.2 sec. The source temperature was set at 120° C. and nitrogen was used as desolvation gas (800 L/h) at 250° C. The voltages of the sampling cone and capillary were 39 V and 3.2 kV, respectively. Reserpine (50 mg/L) was used as the lock spray reference compound (5 ml/min; 10 sec scan frequency).

Data was processed using MZmine software version 0.60 (14). Lipids were identified using internal spectral library. The normalization was performed using multiple internal standards as follows. All monoacyl lipids except cholesterol esters, such as monoacylglycerols and lysophospholipids were normalized with the 1-Heptadecanoyl-2-Hydroxy-sn-Glycero-3-Phosphocholine, all diacyl lipids except phosphatidylethanolamines and ethanolamine plasmalogens were normalized with 1,2-Diheptadecanoyl-sn-Glycero-3-Phosphocholine, the phosphatidylethanolamines and ethanolamine plasmalogens were normalized with 1,2-Diheptadecanoyl-sn-Glycero-3-Phosphoethanolamine, and the triacylglycerols and cholesterol esters with triheptadecanoin.

Tandem mass spectrometry was used for the identification of selected molecular species of lipids. MS/MS runs were performed by using ESI+mode, collision energy ramp from 15 to 30 V and mass range starting from m/z 150. The other conditions were as shown above.

Following the lipidomica analysis and data processing, total 132 lipid molecular species were identified and included in the data analysis.

Partial Least Squares Discriminant Analysis (PLS/DA) (17) revealed drug-specific changes in lipid profiles (FIG. 1). The differences along the first latent variable (LV1), associated with changes due to statin treatment common to the two drugs, are expectedly associated with lowering of triacylglycerols and cholesterol esters in the statin intervention groups (Supplementary material). The differences between the simvastatin and atorvastatin lipid profiles were found in the third latent variable (LV3). Following VIP (variable importance in the projection) analysis, the most important lipid species were identified for each intervention group. The list of loadings in direction of atorvastatin-simvastatin differences (LV3) for most important lipids in simvastatin and atorvastatin groups is shown in FIG. 2. Notably, the main plasma lipid profile differences between the two statins appear lipid-class specific, with upregulation of several phosphatidylethanolamines and long chain triacylglycerols, and downregulation of choline plasmalogens and cholesterol esters in the simvastatin group.

The invention claimed is:

1. A method for determining statin induced myopathy comprising the steps:
   a) providing a biological sample from an individual prior to or during statin treatment,
   b) collecting a lipidomic profile from said biological sample,
   c) comparing said collected lipidomic profile to reference lipidomic markers, wherein a difference between the collected lipidomic profile and the reference lipidomic markers indicates statin induced myopathy, and said reference lipidomic markers have been established by combining a pro-inflammatory muscle tissue gene expression profile with a lipidomic profile associated with high dosage statin treatment.

2. The method according to claim 1, wherein the method is for determining a risk of said individual to develop statin induced myopathy.

3. The method according to claim 1, wherein the method is for determining early warning signs of statin induced myopathy in said individual.

4. The method according to claim 1, wherein the method is for determining statin induced myopathy in individuals showing symptoms of myopathy.

5. The method according to claim 1, wherein the proinflammatory muscle tissue gene expression profile is the pathway of arachidonate 5-lipoxygenase activating protein (ALOX5AP) gene.

6. The method according to claim 1, wherein said reference lipidomic markers are one or more lipid(s) selected from GPCho (0:0/16:0), GPCho (16:0/0:0), GPCho (O-16:2), GPCho (0:0/18:0), GPCho (18:0/0:0), GPCho (0:0/18:1), GPCho (18:1/0:0), GPCho (0:0/18:2), GPCho (18:2/0:0), GPCho(18:3/0:0), GPCho(0:0/20:3), GPCho (20:3/0:0), GPCho(20:4/0:0), GPCho(20:4/0:0), GPCho(22:6/0:0), Cer (d18:1/22:0), DG(36:2), DG(44:12), GPCho(32:0), GPCho (O-32:0), GPCho (32:1), GPCho (O-32:1), GPCho (34:1), GPCho (O-34:1), GPCho (34:2), GPCho (O-34:2), GPCho (34:3), GPCho(O-34:3), GPCho(36:0), GPCho(36:1), GPCho(36:1), GPCho (36:2), GPCho (O-36:2), GPCho (36:3), GPCho (O-36:3), GPCho (O-36:3), GPCho (36:4), GPCho (36:4), GPCho (O-36:4), GPCho (36:5), GPCho (36:5), GPCho (O-36:5), GPCho (38:2), GPCho(38:3), GPCho (38:4), GPCho(38:4), GPCho(38:4), GPCho (O-38:4), GPCho (38:5), GPCho (O-38:5), GPCho (38:6), GPCho(38:6), GPCho(O-38:6), GPCho(38:7), GPCho(O-38:7), GPCho (40:4), GPCho (O-40:4), GPCho (40:6), GPCho (40:7), SM(d18:0/16:0), SM(d18:0/18:0), SMd18:0/24:0), SM(d18: 1/16:0), SM (d18:1/16:1), SM (d18:1/18:0), SM (d18:1/18: 3), SM(d18:1/20:0), SM(d18:1/22:0), SM(d18:1/22:1), SM(d18:1/24:0), SM(d18:1/24:1), GPEtn(36:1), GPEtn(36: 2), GPEtn(38:1), GPEtn(O-38:1), GPEtn(38:2), GPEtn(38: 4), GPEtn (O-38:5), GPEtn (O-38:6), GPEtn (40:4), GPEtn (42:6), GPSer(36:0), ChoE(18:0), ChoE(18:1), ChoE(18:2), ChoE(20:4) ChoE(20:5), TG(46:0), TG(46:1), TG(46:2), TG(48:0), TG(48:0), TG(48:1), TG(48:1), TG(48:2), TG(48: 3), TG(49:1), TG(50:0), TG(50:0), TG(50:1), TG(50:1), TG(50:2), TG(50:2), TG(50:2), TG(50:3), TG(50:4), TG(51: 1), TG(51:2), TG(51:3), TG(52:0), TG(52:1), TG(52:1), TG(52:2), TG(52:2), TG(52:3), TG(52:4), TG(52:5), TG(54: 2), TG(54:2), TG(54:3), TG(54:3), TG(54:4), TG(54:4), TG(54:5), TG(54:6), TG(56:5), TG(56:5), TG(56:6), TG(56: 7), TG(56:8), TG(56:9), and TG58:8).

7. The method according to claim 1, wherein said reference lipidomic markers are one or more lipid(s) selected from GPCho(34:3), GPCho(36:0), GPCho(36:3), GPCho(38:2), GPCho(38:3), GPCho(38:4), GPCho(38:5), GPCho(O-38: 5), GPCho(38:6), GPCho(38:7), GPCho(O-38:7), GPCho (40:6), SM(d18:0/16:0), SM(d18:0/18:0), SM(d18:1/18:0), SM(d18:1/22:0), GPEtn(38:1), GPEtn(40:4), ChoE(18:0), ChoE(18:2), TG(54:2), TG(54:3), and TG(56:5).

8. The method according to claim 1, wherein said reference lipidomic markers are established from a lipidomic profile collected from the same individual as the lipidomic profile of (b) is collected and said reference lipidomic markers are established before said individual start statin treatment.

9. The method according to claim 1, wherein said reference lipidomic marker is established from lipidomic profiles collected from a healthy generalized population.

10. The method according to claim 1, further comprising:
    (d) measuring the expression of the ALOX5AP gene from the biological sample; and
    (e) comparing the measured ALOX5AP gene expression to reference ALOX5AP gene expression, wherein a difference between the measured ALOX5AP gene expression and the reference ALOX5AP gene expression indicates statin induced myopathy.

11. A kit for performing the method according to claim 1, wherein the kit comprises one or more reference lipidomic markers selected from GPCho(0:0/16:0), GPCho (16:0/0:0), GPCho (O-16:2), GPCho (0:0/18:0), GPCho (18:0/0:0), GPCho (0:0/18:1), GPCho (18:1/0:0), GPCho (0:0/18:2), GPCho (18:2/0:0), GPCho (18:3/0:0), GPCho(0:0/20:3), GPCho(20:3/0:0), GPCho(20:4/0:0), GPCho(20:4/0:0), GPCho(22:6/0:0), Cer (d18:1/22:0), DG(36:2), DG (44:12), GPCho (32:0), GPCho (O-32:0), GPCho (32:1), GPCho (O-32:1), GPCho (34:1), GPCho (O-34:1), GPCho (34:2), GPCho (O-34:2), GPCho (34:3), GPCho (O-34:3), GPCho (36:0), GPCho(36:1), GPCho(36:1), GPCho(36:2), GPCho (O-36:2), GPCho(36:3), GPCho(O-36:3), GPCho(O-36:3), GPCho(36:4), GPCho(36:4), GPCho(O-36:4), GPCho(36:5), GPCho(36:5), GPCho(O-36:5), GPCho(38:2), GPCho (38:3), GPCho(38:4), GPCho(38:4), GPCho(38:4), GPCho (O-38:4), GPCho(38:5), GPCho(O-38:5), GPCho(38:6), GPCho(38:6), GPCho(O-38:6), GPCho (38:7), GPCho (O-38:7), GPCho (40:4), GPCho (O-40:4), GPCho (40:6), GPCho (40:7), SM (d18:0/16:0), SM (d18:0/18:0), SMd18:0/24:0), SM(d18:1/16:0), SM(d18:1/16:1), SM(d18:1/18:0), SM (d18:1/18:3), SM (d18:1/20:0), SM (d18:1/22:0), SM(d18:1/22:1), SM(d18:1/24:0), SM(d18:1/24:1), GPEtn (36:1), GPEtn(36:2), GPEtn(38:1), GPEtn(O-38:1), GPEtn (38:2), GPEtn(38:4), GPEtn(O-38:5), GPEtn(O-38:6), GPEtn(40:4), GPEtn(42:6), GPSer(36:0), ChoE(18:0), ChoE (18:1), ChoE(18:2), ChoE(20:4), ChoE(20:5), TG(46:0), TG(46:1), TG(46:2), TG(48:0), TG(48:0), TG(48:1), TG(48:1), TG(48:2), TG(48:3), TG(49:1), TG(50:0), TG(50:0), TG(50:1), TG(50:1), TG(50:2), TG(50:2), TG(50:2), TG(50:3), TG(50:4), TG(51:1), TG(51:2), TG(51:3), TG(52:0), TG(52:1), TG(52:1), TG(52:2), TG(52:2), TG(52:3), TG(52:4), TG(52:5), TG(54:2), TG(54:2), TG(54:3), TG(54:3), TG(54:4), TG(54:4), TG(54:5), TG(54:6), TG(56:5), TG(56:5), TG(56:6), TG(56:7), TG(56:8), TG(56:9), and TG58:8).

* * * * *